United States Patent [19]

Sakuma et al.

[11] Patent Number: 5,084,242

[45] Date of Patent: Jan. 28, 1992

[54] DISTRIBUTION NOZZLE APPARATUS FOR AUTOMATIC CHEMICAL ANALYZER

[75] Inventors: Yoshihiro Sakuma, Tochigi; Hitoshi Shivutani, Ootawara, both of Japan

[73] Assignee: Kabushiki Kaisha Toshiba, Kawasaki, Japan

[21] Appl. No.: 628,992

[22] Filed: Dec. 17, 1990

Related U.S. Application Data

[63] Continuation of Ser. No. 231,399, Aug. 12, 1988, abandoned.

[30] Foreign Application Priority Data

Aug. 14, 1987 [JP] Japan .................. 62-202748

[51] Int. Cl.$^5$ .................................................. B01L 3/02
[52] U.S. Cl. ........................................... 422/100; 422/63; 422/64; 422/65; 422/67; 73/864.25
[58] Field of Search .................. 364/498, 499, 800; 73/864.23, 864.24, 864.25; 422/100, 63, 64, 65, 66, 67; 436/43

[56] References Cited

U.S. PATENT DOCUMENTS

| | | | |
|---|---|---|---|
| 3,858,450 | 1/1975 | Jones | 422/100 |
| 4,076,503 | 2/1978 | Atwood et al. | 422/100 |
| 4,311,067 | 1/1982 | Gocho | 422/64 |
| 4,322,216 | 3/1982 | Lillig et al. | 73/864.25 |
| 4,343,766 | 8/1982 | Sisti et al. | 422/63 |
| 4,344,768 | 8/1982 | Parker et al. | 73/864.25 |
| 4,774,055 | 9/1988 | Wakatake et al. | 422/64 |
| 4,781,891 | 11/1988 | Galle et al. | 422/64 |

Primary Examiner—Robert J. Warden
Assistant Examiner—Laura E. Collins
Attorney, Agent, or Firm—Oblon, Spivak, McClelland, Maier & Neustadt

[57] ABSTRACT

In an automatic chemical analyzer, a plurality of reagent containers are arranged annularly in a table and a reagent distribution nozzle unit is located between reaction cells and reagent containers and substantially at the center of an arcular array of container. In the nozzle unit, arm is secured to shaft which is vertically displaceable and rotatable. The arm is provided with a tiltable arm head and a nozzle for withdrawing a reagent from the reagent container is fixed to the arm head. The arm head and nozzle is tilted and a suction port of nozzle is shifted from a position over the reagent container to a position over draining groove, when the shaft is rotated.

6 Claims, 4 Drawing Sheets

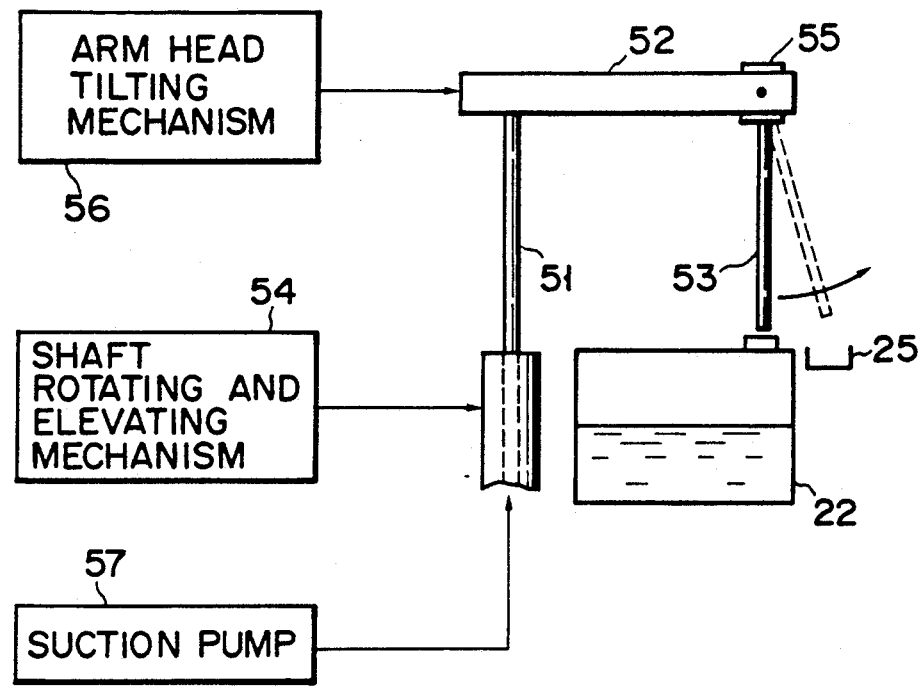
F I G. 2
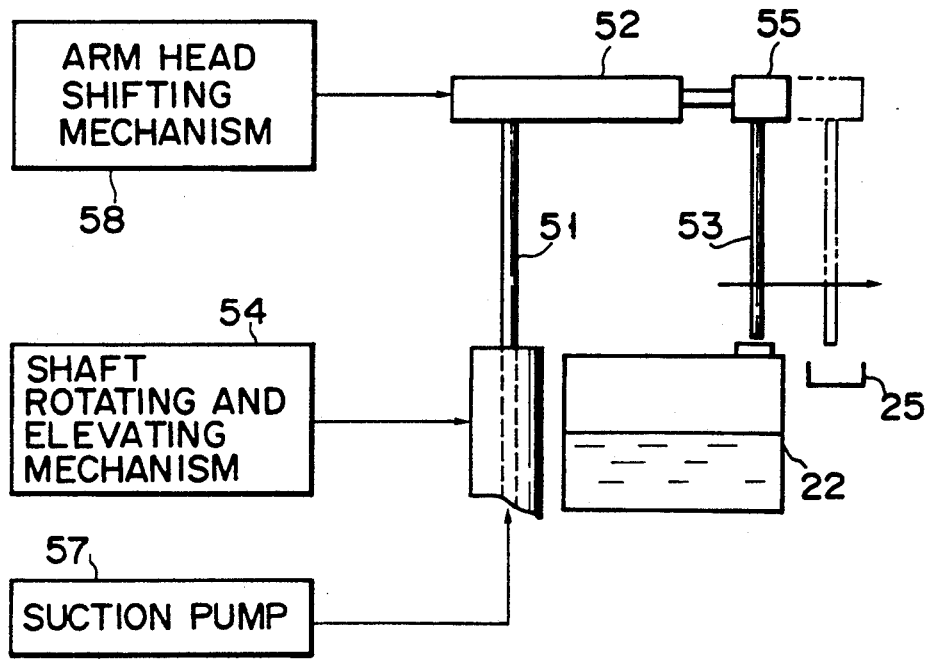
F I G. 4

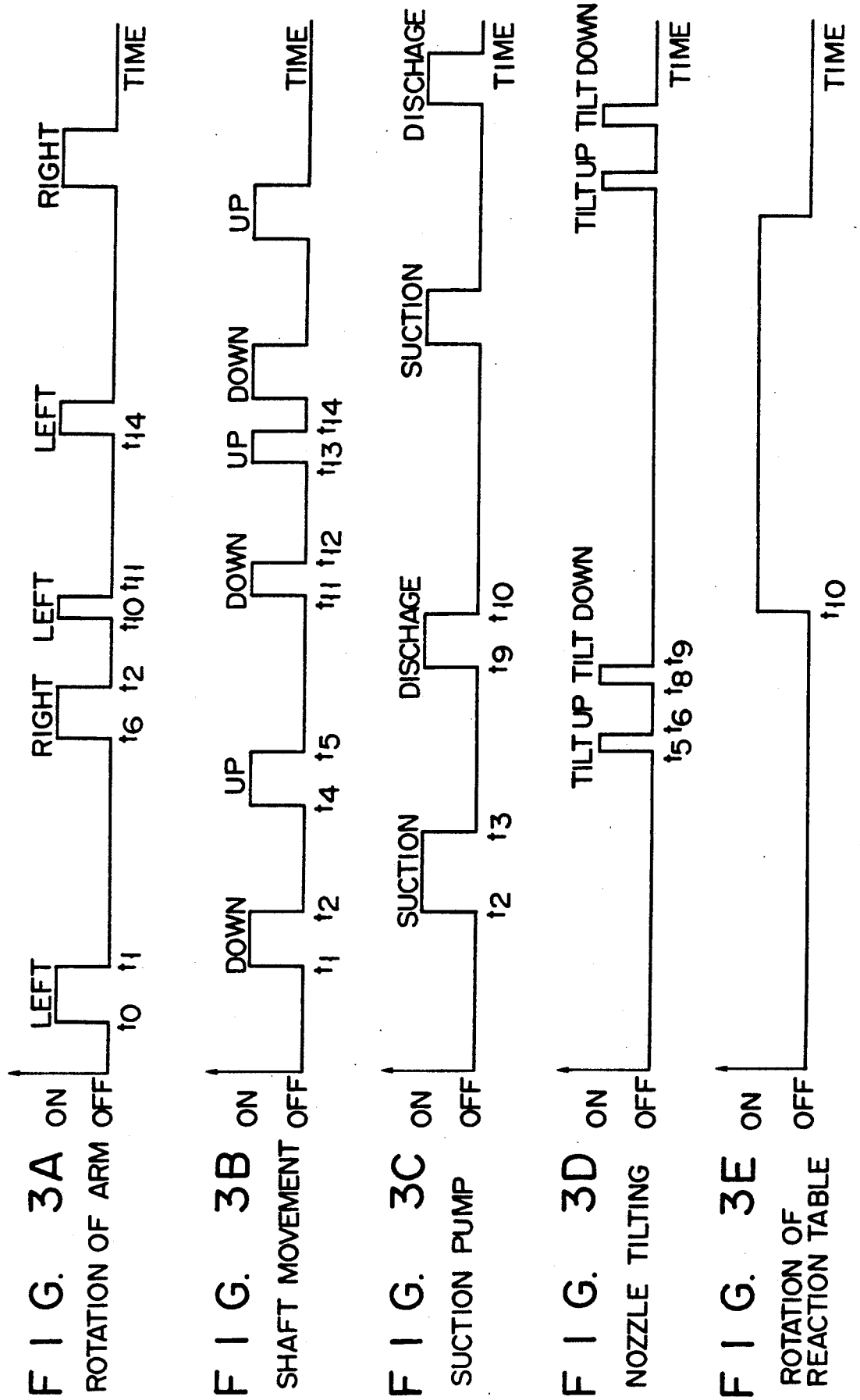

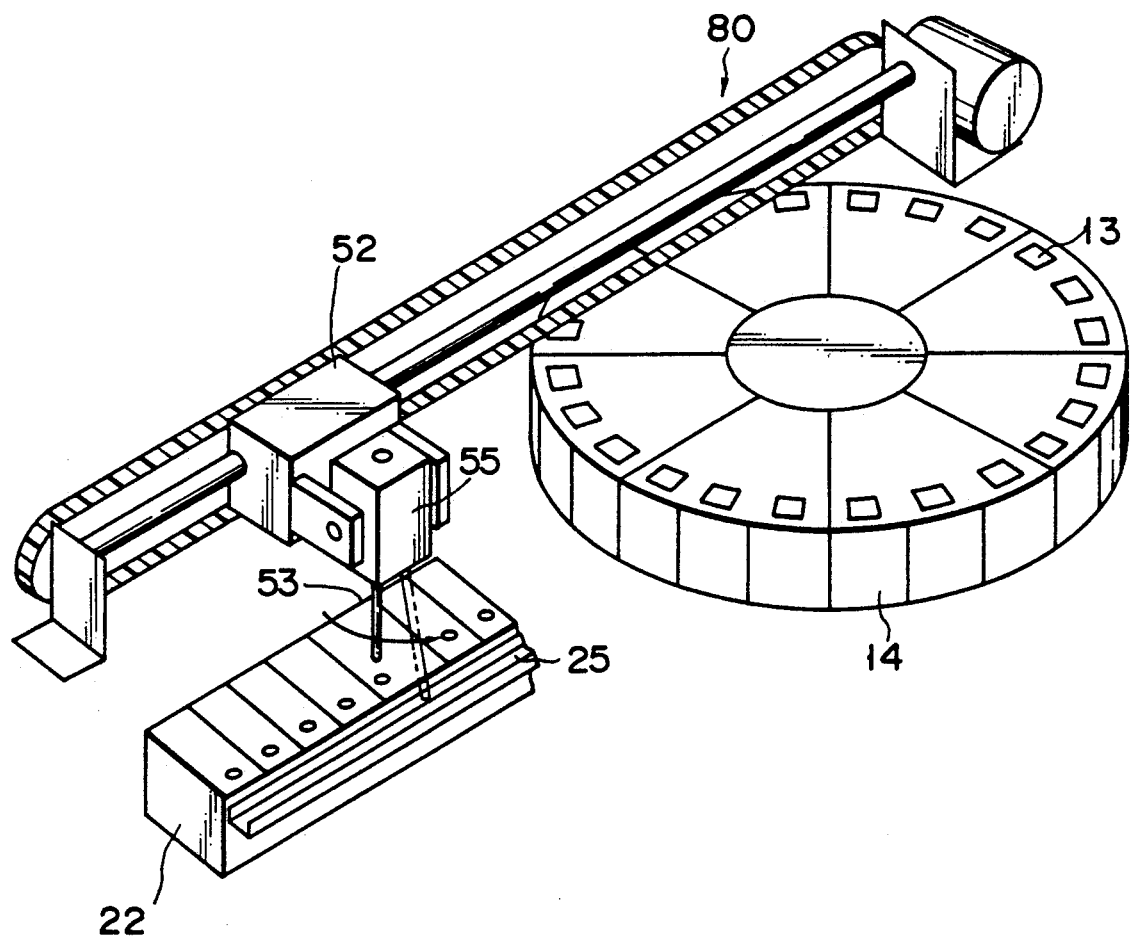
F I G. 5

DISTRIBUTION NOZZLE APPARATUS FOR AUTOMATIC CHEMICAL ANALYZER

This application is a continuation of application Ser. No. 231,399, filed on Aug. 12, 1988, now abandoned.

BACKGROUND OF THE INVENTION

1. Field of the Invention

This invention relates an automatic chemical analyzer used in the field of medical examination and, more particularly, to improvements in the distribution nozzle apparatus in the automatic chemical analyzer.

2. Description of the Related Art

Recently, various medical examinations, e.g., examinations of the blood and urine are indispensable for medical diagnosis, and automatic chemical analyzers are used for these examinations. In an automatic chemical analyzer, a sample of blood or the like is distributed in reaction cells capable of movement in a temperature-maintained reaction tank by a sample distribution nozzle apparatus, and also a reagent for reaction is distributed to the reaction cells containing the sample by a reagent distribution nozzle apparatus. The sample and reagent are reacted for a predetermined period of time in each reaction cell held in a temperature-maintained state. Subsequently, the light transmittivity or absorbance of the liquid under examination obtained after the reaction is measured by an optical measuring system. The absorbance thus measured is analyzed for examination of the sample.

In a usual distribution nozzle apparatus, e.g., a reagent distribution nozzle apparatus, assembled in such an automatic chemical analyzer, an arm is supported for revolution on a shaft provided at the center of an annular array of a plurality of reagent containers, and a distribution nozzle is secured to a free end of the arm. In a distributing operation of such a distribution nozzle apparatus, the distribution nozzle is introduced into a specified reagent container to withdraw a predetermined quantity of reagent therefrom, and then it is retreated from the reagent container and transferred along an orbit extending above the reagent container array to a position above a specified reaction cell for distributing a predetermined quantity of reagent to the reaction cell.

In such a distribution nozzle apparatus, during the reagent withdrawing operation a small quantity of reagent attached to the nozzle end drops during revolution of the nozzle. The dropping reagent is frequently liable to enter a different reagent container to cause mixture of different reagents. For this reason, in the prior art distribution nozzle apparatus a shutter is provided in the vicinity of each reagent container such that the opening of the reagent container is closed by the shutter. When and only when withdrawing a particular reagent from a specified reagent container, the associated shutter is retreated to open the opening of the reagent container to introduce the nozzle thereinto. When the particular reagent is withdrawn by the nozzle and it is ready to cause revolution of the arm, the openings of all the reagent containers are closed by the respective shutters, and the distribution nozzle having withdrawn the reagent is revolved above the shutters toward the reaction cell. In such a distribution nozzle apparatus with the shutters, if a slight quantity of reagent attached to the nozzle at the time of the reagent withdrawal drops during the nozzle revolution, it falls on a shutter and never enters any reagent container. Thus, it is possible to avoid occasional mixture of different reagents.

With such distribution nozzle apparatus with the shutters provided for prevention of the mixing of different reagents, the shutters are each provided in the vicinity of each reagent container and are required to be operated in a predetermined timed relation to the operation of the distribution nozzle. Therefore, the construction of the distribution nozzle apparatus inevitably becomes complicated and elaborate. Besides, there is a possibility that a chemical falling on a shutter enters a mechanical part thereof and then crystallizes, thus causing an erroneous operation. In order to maintain the accuracy of the distribution nozzle apparatus, the operation of cleaning the shutters is indispensable, and a design of apparatus giving consideration to the maintenance is required. Further, the maintenance itself is a considerable burden to the operator. The above problems are also presented in case of a sample distribution apparatus which is used for a sample-distributing operation.

SUMMARY OF THE INVENTION

An object of the invention is to provide a distribution nozzle apparatus for an automatic chemical analyzer, which has a mechanically simple construction and can prevent mixing of different reagents or samples.

According to the invention, there is provided an apparatus for distributing a solution to reaction cells for reaction therein, comprising:

solution-containing means including containers each containing a solution and having an opening, said openings being arranged in an array;

nozzle means having a suction port for withdrawing a solution from each of said containers through said opening and holding the withdrawn solution; and transporting means for transporting said nozzle means with said withdrawal opening held retreated out of said array of openings of said containers from one of said containers to a reaction cell.

BRIEF DESCRIPTION OF THE DRAWINGS

FIG. 2 is a schematic representation of the embodiment of the distribution nozzle apparatus shown in FIG. 1;

FIGS. 3A to 3E constitute a timing chart illustrating the operation of the distribution nozzle apparatus shown in FIGS. 1 and 2 and related mechanism;

FIG. 4 is a schematic representation of a different embodiment of the distribution nozzle apparatus according to the invention; and FIG. 5 is a perspective view showing a modification of the automatic chemical analyzer incorporating one embodiment of the distribution nozzle apparatus according to the invention.

DETAILED DESCRIPTION OF THE PREFERRED EMBODIMENTS

Figure 1:
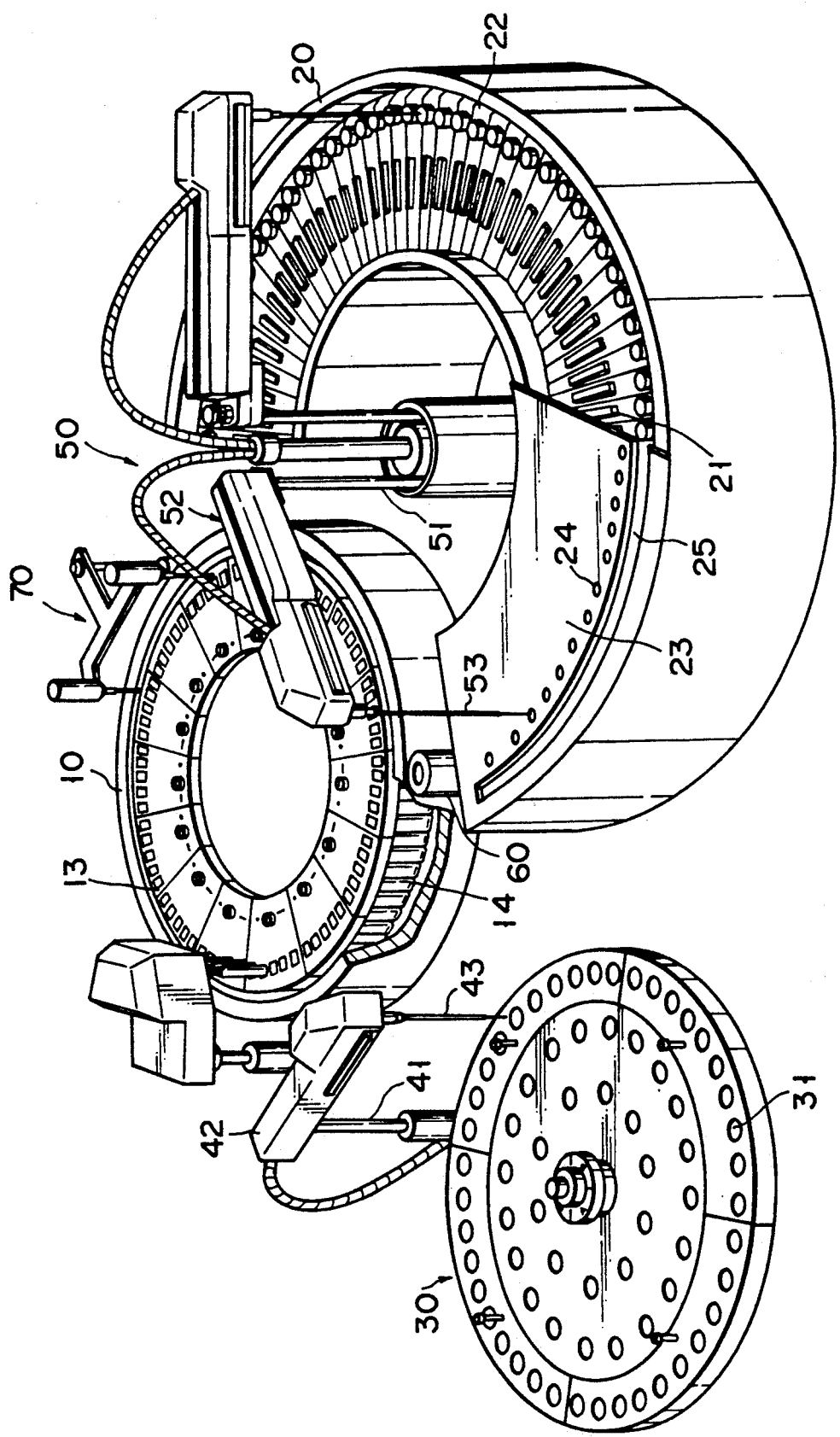
FIG. 1 is a perspective view showing an automatic chemical analyzer incorporating an embodiment of the distribution nozzle apparatus according to the invention.

FIG. 1 is a perspective view showing an automatic chemical analyzer incorporating an embodiment of the distribution nozzle apparatus according to the invention. In the automatic chemical analyzer shown in FIG. 1, reaction table 13 is provided rotatably in temperature-maintained tank 10. A plurality of reaction cells 14 are set in reaction table 13. Near temperature-maintained table 10, reagent table 20 and rotatable sample table 30 are disposed. Reagent table 20 has table top 21, in which a plurality of reagent containers 22 are arranged annularly. Like-wise, a plurality of sample containers 31 are arranged in sample table 30. Sample distribution nozzle unit 40 is provided between sample table 30 and temperature-maintained tank 10. Also, a pair of reagent distribution nozzle units 50 are provided between temperature-maintained tank 10 and reagent table 20 and substantially at the center of an arcuate array of reagent containers 22.

In sample distribution nozzle unit 40, arm 42 is secured to shaft 41, which is vertically displaceable by a lift mechanism (not shown) and also rotatable by a rotating mechanism (not shown). The free end of arm 42 is provided with nozzle 43, which has a suction port for withdrawing a sample from given sample container 31. Nozzle 43 is coupled to a suction pump (not shown).

In each of reagent distribution nozzle units 50, as shown in FIG. 2, like in sample distribution nozzle unit 40, arm 52 is secured to shaft 51, which is vertically displaceable and rotatable by lifting/rotating mechanism 54. Arm 52 has arm head 55 supported at its free end such as to be tiltable about a horizontal axis by arm head tilting mechanism 56, which comprises shifting means and consists of a solenoid and a spring mechanism. Arm head 55 is provided with nozzle 53 for withdrawing a reagent from given reagent container 22.

As shown in FIG. 1, cover 23 is provided over reagent table 21, and it has holes 24 each corresponding in position to the opening of each reagent container 22. It has draining gutter or groove 25 formed on the outer side of the array of holes 24 and along an orbit of the end of nozzle 53 traced when each arm 52 is rotated. Cleaning vessel 60 containing a liquid for cleaning nozzle 53 is disposed along an orbit traced by the end of nozzle 53 when each arm between reagent table 20 and temperature-maintained tank 10 is rotated.

Now, the operation of distribution nozzle units 40 and 50 shown in FIGS. 1 and 2 will be described.

First, sample distribution nozzle unit 40 is operated to distribute samples to given reaction cells 14. More specifically, in sample distribution nozzle unit 40 shaft 41 is rotated by the rotating mechanism according to a command from a control circuit (not shown), thus causing revolution of arm 42 to bring nozzle 43 to a position corresponding to given sample container 31. When nozzle 43 is brought to a position corresponding to given sample container 31, shaft 41 is lowered by the lift mechanism according to a command from the control circuit, thus causing nozzle 43 to enter sample container 31. When the withdrawal opening of nozzle 43 reaches the liquid surface of the sample contained in sample container 31, the reaching of the liquid surface by nozzle 43 is detected in a manner as disclosed in U.S. Pat. No. 4,818,492, and the suction pump is operated. As a result, a predetermined quantity of sample is withdrawn from container 31 into nozzle 43 through the suction port. When the withdrawal is ended, shaft 41 is raised. Then, shaft 41 is rotated to cause revolution of arm 42 so as to bring nozzle 43 to a position above given reaction cell 14. Over given reaction cell 14, the sample is discharged from nozzle 43 into reaction cell 14. In this way, given sample is distributed to given reaction cells 14.

While sample distribution nozzle unit 40 is distributing a given sample to given reaction cells 14, reagent distribution nozzle units 50 are operated. Since the two reagent distribution nozzle units 50 are operated substantially in the same way, the operation of only one of these units will be described for the sake of brevity. Shaft 51 of reagent distribution nozzle unit 50 is rotated counterclockwise, i.e., to the right, in FIG. 1 from instant t0 as shown in FIG. 3A by a drive signal from controller (not shown). This rotation of shaft 51 causes revolution of the arm to bring nozzle 53 to a position over specified reagent container 22 as shown in FIG. 2. Then, at instant t1 as shown in FIG. 3B, lift mechanism 54 is operated to lower shaft 51 so as to cause nozzle 53 to enter specified reagent container 22. When the reaching of the liquid surface of the reagent by nozzle 53 is detected in the manner as described before, and the nozzle is immersed in the reagent, suction pump 57 as shown in FIG. 2 is operated for a period from instant t2 to instant t3 as shown in FIG. 3C to cause withdrawal of the reagent into nozzle 53. In this way, a predetermined quantity of reagent is retained in nozzle 53. When the withdrawal is completed, lift mechanism 54 is operated again from instant t4 in FIG. 3B, thus raising shaft 51 so that nozzle 53 is retreated out of reagent container 22. At instant t5 of completion of the retreat of nozzle 53, arm head tilting mechanism 56 is operated to tilt up nozzle 53. As a result, the suction port of nozzle 53 is shifted from a position over reagent container 22 to a position over draining gutter or groove 25. Once nozzle 53 is tilted up, it is held as such, and in this state shaft 51 is rotated as shown in FIG. 3A, thus causing revolution of arm 52 in the clockwise direction, i.e., to the left. During this revolution, the suction port of nozzle 53 does not trace any orbit vertically above the array of holes 24 of cover 23 corresponding in position to the openings of reagent containers 22. When reagent nozzle 53 has its end brought to a position near specified reaction cell 14 and its stem brought to a position over specified reaction cell 14 with the revolution of reagent arm 52, tilting mechanism 56 is operated again at instant t8 as shown in FIG. 3D to tilt down nozzle 53, and at instant t9 the suction port of nozzle 53 is brought to a position over the opening of specified reaction cell 14. At this instant t9, suction pump 57 is operated to cause discharge of the reagent from nozzle 53 into reaction cell 14. When the discharge of the reagent is completed, reaction table 13 is rotated, and at instant t10 shaft 51 is rotated again to cause revolution to arm head 55 in the counterclockwise direction, i.e., to the right. When nozzle 53 is brought to a position over cleaning vessel or pool 60 at instant t11, shaft 51 is lowered in a period form instant t11 to instant t12 as shown in FIG. 3B, so that nozzle 53 is immersed in a cleaning liquid in vessel or pool 60 and is cleaned. When the cleaning is completed, shaft 51 is raised in a period from instant t13 to instant t14 as shown in FIG. 3B, so that nozzle 53 is retreated out of cleaning vessel or pool 60. At instant t14, nozzle 53 is rotated to the right to a position over specified reagent container 22. In reaction table 13, the reaction cells are progressively brought to a position under agitator 70 with rotation of table 13. Sample and reagent are agitated together by agitator 70 for the reaction of the two. Subsequently, the light transmittivity of the liquid obtained after the reaction is measured optically in the manner as disclosed in U.S. Pat. No. 4,451,433. In this way, the sample is analyzed.

In the above embodiment nozzle 53 for the reagent is tilted up such that the end of nozzle 53 after withdrawal of the reagent traces an orbit over draining groove or gutter, so that it is possible to reliably prevent the reagent dropping from nozzle 53 from entering reagent containers 22. Normally or if necessary, a cleaning liquid may be caused to flow along arcular draining groove or gutter 25. By causing the flow of the cleaning liquid, the dropping reagent will be drained along the draining groove or gutter 25 to the outside of the analyzer, so that it is possible to avoid the contamination thereof.

FIG. 4 shows a different embodiment of the invention. In this instance, instead of causing the tilting of nozzle 53 as in the preceding embodiment, arm head 55 is shifted linearly by arm head shifting mechanism 58 for the movement of the end of nozzle 53 along draining groove or gutter 25.

Further, as shown in FIG. 5, it is possible to assemble the nozzle-tilting mechanism in an automatic chemical analyzer, in which reagent containers 22 are arranged linearly, and arm 52 is supported on and moved linearly by belt mechanism 80 driven by motor 81. Obviously, it is possible to assemble the mechanism as shown in FIG. 4 in the analyzer as shown in FIG. 5.

Further, while the above embodiments have concerned with a case where a mechanism for shifting by tilting or linearly shifting a nozzle is assembled in the reagent distribution nozzle unit, it is obviously possible to assemble the mechanism for tilting or linearly shifting a nozzle in the sample distribution nozzle unit.

As has been described in the foregoing, with the distribution nozzle device according to the invention it is possible to reliably prevent occasional introduction of different reagent or samples into reagents or samples. Further, it is possible to obtain a mechanically simple and rigid structure which can be readily controlled, so that it is possible to extremely improve the accuracy of the analyzer.

What is claimed is:

1. An apparatus for distributing a solution to reaction cells for chemical reaction therein, comprising:

solution-containing means including a plurality of containers each containing a solution and having an opening, said openings being arranged in an array extending along a portion of a transport path;

nozzle means having a suction port positionable for withdrawing a solution from at least one of said containers through said suction port and holding the withdrawn solution;

transport means for moving said nozzle means along the transport path such that said suction port moves in an orbit vertically above said array of said openings; and shifting means including control means for shifting said suction port of said nozzle means away from the orbit vertically above said array of said openings and to a position such that withdrawn solution dripping from said nozzle means during transporting of said nozzle means along said portion of the transport path to a reaction cell does not contaminate solution remaining in said containers, wherein said transport means includes means for transporting said nozzle means with said shifted suction port along another portion of the transport path to a reaction cell to discharge the withdrawn solution.

2. The apparatus according to claim 1, wherein said shifting means includes means for tilting said nozzle means about a horizontal axis and away from the array of said openings.

3. The apparatus according to claim 1, wherein said shifting means comprises means to horizontally shift said suction ports of said nozzle means away from the array of said openings.

4. The apparatus of claim 1, including means for vertically moving the nozzle, whereby the suction port can enter or withdraw from an opening of a given container.

5. The apparatus according to claim 1, wherein the openings of said containers are arranged in a substantially arcuate array.

6. The apparatus according to claim 1, which further comprises:

means extending along the transport path for receiving solution dropping from said suction port.

* * * * *